United States Patent
Clowers et al.

(10) Patent No.: US 10,132,777 B2
(45) Date of Patent: Nov. 20, 2018

(54) TWO-PHASE APPROACH TO FOURIER TRANSFORM ION MOBILITY TIME-OF-FLIGHT MASS SPECTROMETRY

(71) Applicant: WASHINGTON STATE UNIVERSITY, Pullman, WA (US)

(72) Inventors: Brian H. Clowers, Pullman, WA (US); William F. Siems, Spokane, WA (US)

(73) Assignee: WASHINGTON STATE UNIVERSITY, Pullman, WA (US)

( * ) Notice: Subject to any disclaimer, the term of this patent is extended or adjusted under 35 U.S.C. 154(b) by 98 days.

(21) Appl. No.: 15/266,545

(22) Filed: Sep. 15, 2016

(65) Prior Publication Data
US 2017/0074826 A1    Mar. 16, 2017

Related U.S. Application Data

(60) Provisional application No. 62/218,637, filed on Sep. 15, 2015.

(51) Int. Cl.
*G01N 27/62* (2006.01)
*H01J 49/00* (2006.01)
*H01J 49/40* (2006.01)

(52) U.S. Cl.
CPC ........ *G01N 27/622* (2013.01); *H01J 49/0036* (2013.01); *H01J 49/0027* (2013.01); *H01J 49/40* (2013.01)

(58) Field of Classification Search
USPC ....................................................... 702/189
See application file for complete search history.

(56) References Cited

U.S. PATENT DOCUMENTS

| | | | | |
|---|---|---|---|---|
| 4,633,083 A * | 12/1986 | Knorr | ................ | G01N 27/622 250/282 |
| 5,719,392 A * | 2/1998 | Franzen | ............... | G01N 27/622 250/282 |
| 6,300,626 B1 * | 10/2001 | Brock | ................. | H01J 49/0027 250/287 |
| 6,870,157 B1 * | 3/2005 | Zare | ..................... | H01J 49/0027 250/281 |
| 2003/0146392 A1 * | 8/2003 | Kimmel | ................... | H01J 9/14 250/396 R |
| 2007/0041728 A1 * | 2/2007 | Dorrer | ..................... | G01J 11/00 398/16 |
| 2009/0294647 A1 * | 12/2009 | Michelmann | ........ | G01N 27/622 250/282 |
| 2015/0090872 A1 * | 4/2015 | Platt | ..................... | H01J 49/0036 250/281 |

* cited by examiner

*Primary Examiner* — Paul D Lee
(74) *Attorney, Agent, or Firm* — Whitham & Cook, P.C.

(57) ABSTRACT

The methods herein provide for analysis of ion populations. Certain aspects include: obtaining a first data set that includes: a first binary On-OFF frequency sweep across a range of frequencies resulting in a first raw data in the time domain and obtaining a second data set that includes: a second binary On-OFF frequency sweep 180° out of phase from the first binary On-OFF frequency sweep so as to result in a second raw data in the time domain from received ion current resulting from the second binary On-OFF frequency sweep. Thereafter the two data sets are combined to provide for raw mobility signals of the ion populations in the time domain for each m/z over a range of selected m/z values. Additional aspects include a hybrid system for performing the methods disclosed herein.

12 Claims, 7 Drawing Sheets

TWO-PHASE APPROACH TO FOURIER TRANSFORM ION MOBILITY TIME-OF-FLIGHT MASS SPECTROMETRY

CROSS-REFERENCE TO RELATED APPLICATION(S)

The present application claims under 35 U.S.C. § 119, the priority benefit of U.S. Provisional Application No. 62/218,637 filed Sep. 15, 2015. The disclosure of the foregoing application is incorporated herein by reference in its entirety.

GOVERNMENT INTERESTS

This invention was made with government support under grant no. HDTRA1-14-1-0023 awarded by the Department of Defense through the Defense Threat Reduction Agency. The government has certain rights in the invention.

FIELD OF THE INVENTION

The present invention relates to the field of Ion Mobility Mass Spectroscopy (IMMS). More particularly, the present invention relates to a two-phase Ion Mobility Mass spectrometry (IMMS) methodology to enhance sensitivity and acquisition speed for measurements using such instrumentation.

BACKGROUND OF THE INVENTION

Discussion of the Related Art

The utility of ion mobility spectrometry (IMS) for separation of ions has been demonstrated extensively, but IMS combined with mass spectrometry (MS) has remained a niche technique, mainly because of the loss of sensitivity due to ion losses within the combination of techniques. IMS, in particular, remains a needed and desired technique to be coupled with MS because of the speed of the separation technique. Specifically, IMS exploits the beneficial aspect that different particles diffuse through a gas at different speeds, depending on their collision cross-sections with the introduced gas molecules. While neutrals diffuse randomly (via Brownian motion), ions in an applied electric field drift in a defined direction with the velocity controlled by their mobility (K). Such a quantity generally varies with the field intensity E but IMS is often run in a low-field regime where K(E) is substantially constant. In that limit, K depends on the ion/buffer gas collision cross-section $\Omega$, which allows a spatial separation of different ions.

The IMS concept of measuring size-to-charge ratio is also beneficially complementary to the principle of measurement in mass spectrometry (MS) of mass-to-charge ratio (m/z). When combined with MS, ion mobility-mass spectrometry (IMMS) represents a powerful analytical combination capable of distinguishing ions based upon both size and mass-to-charge ratios. A particular beneficial IMS analytical tool is a drift-tube ion mobility spectrometer (DT-IMS) based on the ability to rapidly screen passengers, cargo, and the surrounding environment for narcotics, explosives, and chemical warfare agents. DT-IMS also finds utility as an informative tool to probe gas-phase ion chemistry, kinetics, and under select conditions gas-phase ion conformations. As with many time-dispersive techniques however, challenges related to duty cycle are quite common when utilizing DT-IMS instruments. The duty cycle in most DT-IMS experiments is usually on the order of <1% and this limitation in ion throughput naturally impacts sensitivity. Despite this limitation, a suite of vendors have begun producing a range of mobility-based instruments, including DT-IMS systems, for the research community, and this access has further propelled adoption of the technique. While these ion mobility-mass spectrometry (IMMS) instruments enable a broad class of researchers, they are still limited by duty cycle which constrains their ultimate potential. These classic trade-offs are by no means new problems, but few solutions have been wholly adopted by the community.

Particular solutions applied to combat the duty cycle problem include multiplexing approaches such as Fourier and Hadamard pulsing schemes, which have been shown to independently enhance the throughput of ion mobility spectrometry (IMS) experiments. Historically however, FT-IMS experiments, for example, never realized the full Signal to Noise Ratio (SNR) potential suggested by theory. As a result, challenges nonetheless remain as to the broad scale implementation using such techniques when utilized with ion mobility mass spectrometry (IMMS) instruments.

Accordingly, a need exists for providing a hybrid ion mobility single gate time-of-flight system that incorporates modulating the ion beam via a single ion gate using two frequency chirps oriented 180° out of phase. Such a system is beneficially combined with transform (e.g., FT-IMMS, Hadamard-IMMS) methodologies that enhances both signal-to-noise ratios (SNR), ion throughput, and does not require any hardware modifications. The present embodiments herein addresses such a need.

SUMMARY OF THE INVENTION

A particular aspect of the embodiments herein is directed to a method of ion populations analysis that includes: obtaining a first data set that further comprises: modulating a single ion gate with a first binary On-OFF frequency sweep across a range of frequencies, and acquiring a first raw data in the time domain at a detector from ion current resulting from the first binary On-OFF frequency sweep, obtaining a second data set that further comprises: modulating the single ion gate with a second binary On-OFF frequency sweep across a range of frequencies, wherein the second binary On-OFF frequency sweep is 180° out of phase from the first binary On-OFF frequency sweep, and acquiring a second raw data in the time domain from received ion current resulting from the second binary On-OFF frequency sweep; and combining the first and the second data set to provide for raw mobility signals of the ion populations in the time domain for each m/z over a range of selected m/z values.

Accordingly, the methodologies herein provide for enhances both signal-to-noise ratios (SNR), ion throughput, and does not require any hardware modifications.

DETAILED DESCRIPTION

Figure 1:
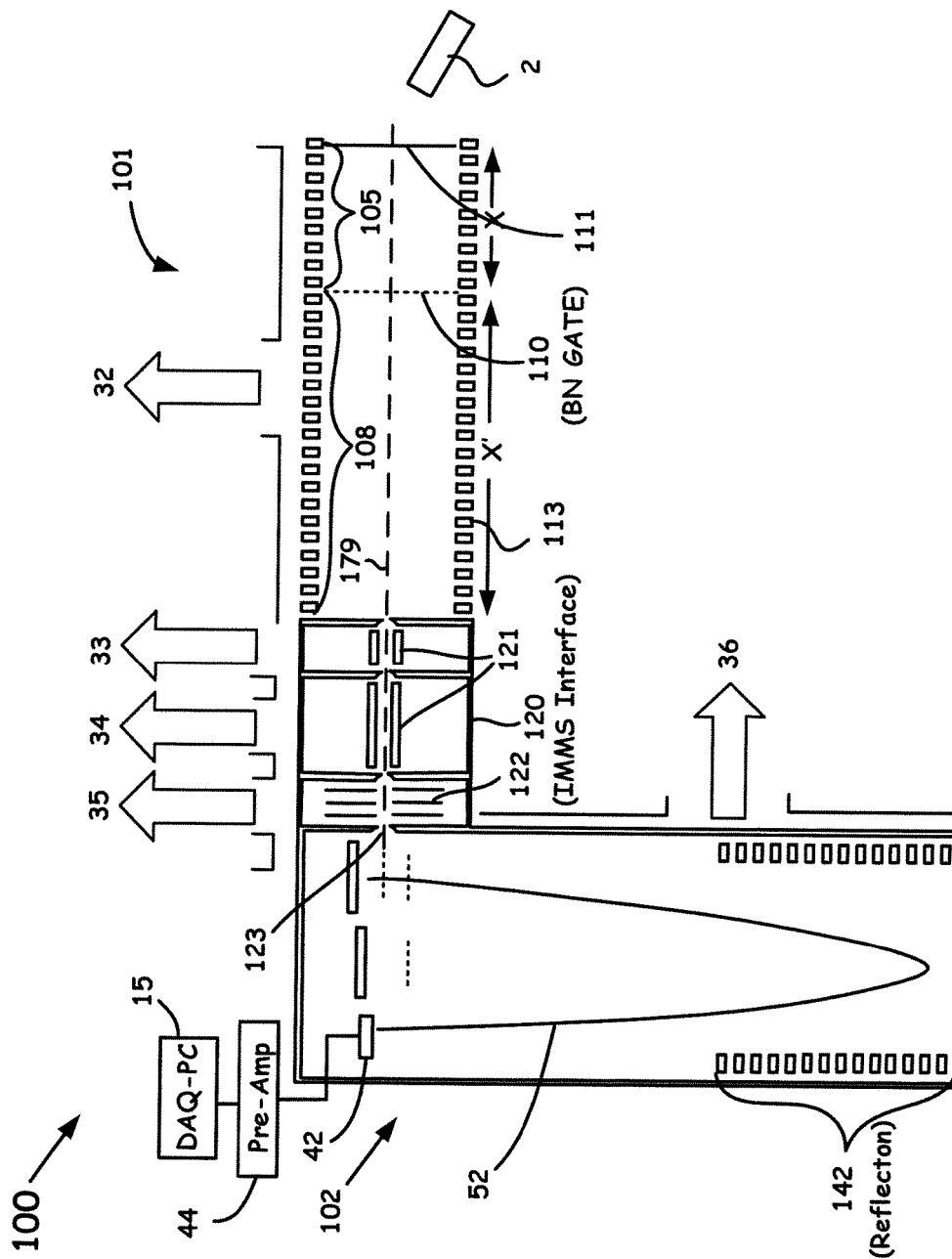
FIG. 1 illustrates an example embodiment of an Atmospheric Pressure Single gate Ion Mobility instrument interfaced to a Compact Time of Flight Mass Spectrometer.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

The embodiments herein are directed to multiplexing transform methods of interpreting ion data (negative and/or positive ions), using, for example, Fourier transform (FT) and Hadamard transform methods configured to be coupled with Ion Mobility Spectrometer (IMS) hybrid arrangements, often but not necessarily, with IMS hybrid arrangements that include drift tube ion mobility mass spectrometers (DT-IMMS). The novel approach herein requires only a single gate and circumvents the need for signal apodization (i.e., a mathematical transformation carried out on data before, e.g., the Fourier transformation), by combining data from two frequency pulsing sequences (i.e., chirped pulsed sequences) 180 degrees out of phase.

In particular, the pulsing sequences utilized herein is based on modulating a single ion gate disclosed herein and thus the ion currents, with two separate in time pulsing sequences 180 degrees out of phase with one another in a binary ON and OFF scheme. The modulation frequency for both of the pulsed sequences are beneficially varied as a time function, a technique known in the art as Chirping. In general, a chirp is a signal in which the frequency increases or decreases with time. The modulation frequency can thus vary monotonically in either direction. Often, the term chirp is used interchangeably with a frequency sweep signal. Such a chirped pulse can be a continuous function with a phase function that varies slowly in time compared to the amplitude function. As often but not necessarily utilized herein, a linear chirp is applied wherein the frequency increases linearly with time but it is understood that the chirp (frequency sweep) can also be non-linear (e.g., exponential). The binary ON and OFF modulation scheme disclosed herein can also be configured to manipulate the phase, amplitude, or the frequency in a continuous and/or in a non-continuous manner.

Often in operation, a controller/PC controls the application of the applied frequency sweeps (a first binary ON and OFF 0° frequency sweep signal and a second 180° out of phase binary ON and OFF frequency sweep signal) for the ion gate and processes the collected ion current signal in time. Importantly, the scheme disclosed herein requires the acquisition of two data sets (both modulation (a frequency sweep) and raw data sets) prior to applying, for example the Fourier transform (e.g., a Fast Fourier transform (FFT)) so as to obtain ion population (mobility) information. If desired, the methodology can be applied a number of times to further improve sensitivity. As a result, the method and system disclosed herein improves the signal-to-noise ratio, and thus the detection sensitivity, by up to and often greater than an order of magnitude.

In particular, the surprising results disclosed herein show an unexpected increase in signal-to-noise (SNR) of up to an order of magnitude and even greater relative to both implementations that utilize FT-IMS experiments and signal averaged (SA) experiments. As a prime but not sole example, select tetraalkylammonium salts SNR improvements of more than one order of magnitude have been obtained. To explore the performance metrics associated with the technique, a number of experimental variables were systematically altered including frequency sweep range, sweep time, and data acquisition time.

Accordingly, a basis of the present invention is directed to providing a two-phase FT-IMMS technique to enhance sensitivity for IMMS measurements and to enhance the acquisition speed for mobility measurements using hybrid instrumentation.

Specific Description

FIG. 1 illustrates an example embodiment of an Atmospheric Pressure Single gate Ion Mobility system interfaced to a Compact Time of Flight Mass Spectrometer, as generally designated by the reference numeral 100, configured to operate according to aspects of the configurations disclosed herein. While the system 100 of FIG. 1 is beneficial for illustrative purposes, it is to be understood that other alternative commercial and custom configurations and having various other components, as known and as understood by those in the field of ion mobility and mass spectroscopy, can also be incorporated when using the Two-Phase Approach disclosed herein.

It is to be appreciated that while not all elements of the system 100 shown FIG. 1 are denoted for simplicity, the components of note include an ion source 2, an ion mobility spectrometer 101, and a time-of-flight spectrometer 102, with the ion mobility spectrometer (IMS) 101 comprising a heated desolvation region 105 as known in the art having a length X, a drift region 108 having a length X', an ion gate 110 (e.g., a Bradbury-Nielsen ion gate) and an Ion Mobility Mass Spectrometer Interface (IMMS) 120.

From such an arrangement, a sample containing one or more analytes of interest can initially be ionized via ion source 2 using any of the applicable techniques known and understood by those of ordinary skill in the art. While FIG. 1 depicts an Electrospray Ionization (ESI) configuration as the example ion source 2, a variety of other configurations to provide ions of interest can also be incorporated, such as, but not limited to, Atmospheric Pressure Ionization (API), Atmospheric Pressure Chemical Ionization (APCI), Nano-electrospray Ionization (NanoESI), thermospray ionization, electron impact (EI) ionization, chemical ionization (CI) source, an EI/CI combination ionization source or any other source that can be utilized without departing from the scope of the invention.

Moreover resultant ions are urged through a series of chambers of progressively reduced pressure with a number of ion optics utilized, as known in the art, that operationally guide such ions to provide desired transmission efficiencies. As generally shown in FIG. 1, the various chambers communicate with corresponding ports 32, 33, 34, 35, and 36 (represented as arrows in the figure) that are coupled to a set of pumps (not shown) to maintain the pressures at the desired values. Non-limiting example pressures are 760 Torr or greater for chamber(s) coupled to port 32, 3 Torr for chamber coupled to port 33, $10^{-3}$ Torr for chamber coupled to port 34, $10^{-6}$ Torr for chamber coupled to port 35, and $10^{-7}$ Torr for chamber coupled to port 36. A non-limiting example desolvation length X is at about 10 mm and an example length for the drift region X' is at about 21.5 mm for the IMS portion 101 shown in FIG. 1.

In general operation, ions generated by the ion source 2 are pulsed through the ion gate 110, which is often a configured Bradbury-Nielsen (BN) ion gate. In general, the gate 110 herein is a configured grid of closely arranged wires alternately supplied with different potentials. The ions are attracted to the wires having configured potentials and thus are discharged so as to block ion current. If the system 100 as per the controller/PC 15 as shown in FIG. 1, removes the potentials, the gate 110 is switched to be an open state wherein the ions enter the drift region 108 and are pulled through the drift region by the electric field as provided by the ring electrodes 113 (one denoted for simplicity). However, while a BN ion gate 110 is a desired configuration, it is to be understood that other gate types known in the art can also be utilized, such as, but not limited to, a Tyndall switch, an electric potential well, or a MALDI configuration (i.e., using photoionization), or even configuring an ESI source to be modulated in conformity with the two-phase embodiment disclosed herein.

As noted above, a controller/PC 15 provides the signals for the gate 110 modulation operation (frequency sweep) and is used to interpret the information enabled by the coupled time-of-flight (TOF) instrument 102. While a TOF 102 is shown in FIG. 1, of which can include a reflectron 142, other types of mass spectrometers (e.g., a quadrupole mass analyzer, a two-dimensional ion trap, a three dimensional ion trap, and a linear time-of-flight (TOF) device, etc.) may alternatively be utilized. With respect to the TOF 102 as shown in FIG. 1, as ions enter the TOF and directed along a path 52, ion current is received via the detector 42 (e.g., a multi-channel plate) and amplified (i.e., via pre-map 44). Thereafter, via controller/PC 15, the amplified ion current signal is stored as digitized information and processed using the transformation methods disclosed herein, e.g., using Fourier and/or Hadamard transforms or other methodologies (e.g., Barker code) known and understood by those of ordinary skill in the art.

The controller/PC and data acquisition system itself (generally referenced by the numeral 15) is to be noted of various circuitry of a known type. Such a control and data system can be implemented as any one of or a combination of general or special-purpose processors (digital signal processor (DSP)), firmware, software, graphical user interfaces (e.g., LabVIEW) and/or hardware circuitry to provide instrument control, RF and DC power, and data analysis, etc., for the example configurations disclosed herein.

It is also to be appreciated that instructions to operate the system shown in FIG. 1, which include the enabling of desired RF and DC voltages, the control of pressure via pumping means known in the art, the identifying of m/z values, drift times, cross-sectional areas of the ions, the merging of data, the exporting/displaying/outputting to a user of results, etc., may be executed via for example the controller/PC 15, which includes hardware and software logic for providing the instructions and control functions of the system 100.

In addition, such instructions and control functions, as described above, can also be implemented by the system 100, as shown in FIG. 1, configured to operate via a machine-readable medium (e.g., a computer readable medium). A computer-readable medium, in accordance with aspects of the present invention, refers to media known and understood by those of ordinary skill in the art, which have encoded information provided in a form that can be read (i.e., scanned/sensed) by a machine/computer and interpreted by the machine's/computer's hardware and/or software.

In the general operation of the system 100 shown in FIG. 1, the ion source 2, often an electrospray ionization source (ESI), configured at about 45 degrees provides desired ions. Such ions are gated (allowed to pass) using any number of known in the art gates (e.g., a Tyndall, Bradbury-Neilsen gate, etc., shown generally referenced as numeral 111) into the desolvation region 105 to substantially remove water clusters and desolvate gaseous analytes so as to aid in improving signal-to-noise within a given MS spectrum. The desolvation of ions may be aided by a constant counter current flow between 0.1-10 L/min of gas held at 50-500° C. Any gas (or mixtures thereof) suitable for use in an IMS instrument may be utilized in practice of aspects of the invention, such as, but not limited to Nitrogen, Carbon Dioxide, Oxygen, Nitrous Oxide, Noble Gasses, Sulfur hexafluoride, and combinations thereof.

As shown generally in FIG. 1, the drift region 108 as well as the desolvation region 105 includes electrodes 113 configured as differing sets of conducting drift rings, of which were often wider rings utilized for the desolation region (105) and thinner conducting rings for the drift region (108). Ions are thereafter admitted into the drift region 108 using gate 110, as directed by the system using the novel two phase modulation approaches detailed herein below. Such admitted ions can then move (drift) with individual characteristic velocities within the drift region 108 which is often, as stated above, about 21.5 mm in length under a constructed electric field provided by the electrodes 113.

After exiting the drift region 108, ions are directed to a reduced pressure region interface (i.e., the chamber coupled to port 33) referred to overall as the Ion Mobility Mass Spectrometer Interface (IMMS interface 120). As generally shown in FIG. 1, the IMMS interface 120 includes electrode guides (e.g., quadrupoles 121 and ion optics 122) for urging the ions of which eventually are directed through a pinhole (generally referenced by numeral 123) before being received by the TOF 102 shown in FIG. 1. It is to be noted that the configuration of system 100 shown in FIG. 1 shows an axis 179 for the IMS 101 perpendicular to the TOF 102 instrument and thus perpendicular to the flight ion flight path 52. While such a configuration is beneficial in some aspects, e.g., ion packets entering the ion acceleration region of the TOF 102 are more likely to have constant and more defined initial ion positions, it is also to be noted non-perpendicular configurations can also be utilized without departing from the scope of the invention.

Thereafter, as known to those of ordinary skill in the art, TOF 102 operates to separate ions in time according to their individual masses. Generally, ions having less mass will reach the detector 42 faster than those having greater mass. The detector 42 is configured to receive arrival times of the ions and provide signals corresponding to such ions wherein the controller/PC thereafter can then operate on the received signals using transformation methodologies utilized herein. In general, using the multiplexing two-phase approach, a 50% duty cycle of the generated ions can be realized (in contrast to standard <1% duty cycle) so as to increase overall ion transmission. Moreover, in combination with the transformation of the data (post processing) herein, a signal to noise S/N of at least an order of magnitude is achieved.

To aid the reader in understanding the possible various embodiments of the present invention, the following provides reference when considering designing the Atmospheric Pressure Ion Mobility Time-of-Flight Mass Spectrometer instrument in combination with the modulation and transformation methodologies herein, which is intended to be illustrative only, but not limiting thereof.

EXAMPLE

Atmospheric Pressure Ion Mobility Time-of-Flight Mass Spectrometer

Fourier multiplexing experiments were conducted using an example custom atmospheric pressure ion mobility system 100, as shown in FIG. 1, interfaced to a compact time of flight mass spectrometer (TOF-MS, TOFWERK, Thun, Switzerland). This instrument/system 100, based upon a stacked-ring drift tube design, as briefly discussed above, is capable of operation from ~100 to 250° C. with a homogeneous electric field of ~350 V/cm used in these experiments. Counter-current flow of high-purity, dry nitrogen was introduced at the exit of the drift cell at ~1 L/min and atmospheric pressure (~690 Torr in Pullman, Wash.). Following ionization using an electrospray ionization source (ESI) 2, ions traversed a short desolvation region (~10 cm) before encountering a Bradbury-Nielsen ion gate (BN-gate) 110.

The circular BN-gate 110 frame was constructed using two 99% alumina rings (50 mm ID×58 mm OD×3.5 mm thick) that served to hold two electrically isolated sets of parallel wires made of Alloy-46 (California Fine Wire Co., Grover Beach, Calif.). The wire was approximately 75 µm in diameter and the spacing of the BN-gate 110 was 0.64 mm. The entire gate assembly was held together using a high temperature ceramic epoxy supplied from Cotronics (Resbond 940, Brooklyn, N.Y.).

The choice of materials for the BN-gate 110 enabled matching the thermal coefficients of expansion to maintain gate integrity. Symmetric pulsing of the BN-gate (+/−45 20 V) was accomplished using a custom floating power supply which enabled ions to enter the 23 cm-long drift tube connected to the TOF-MS 102. Serving as the detector, this mass spectrometer 102 acquired full mass spectra (0-1200 m/z) in 60 µs for a sampling rate of 23 16,667 kHz. Signal averaging experiments utilized ion gate pulse widths ranging from 120-360 µs and ion mobility scan times of ~90 ms.

Fourier transform spectra were obtained by sweeping the ion gate 110 opening frequency from a minimum of 5 Hz up to a maximum of ~40 kHz. More specifically, the terminal frequencies examined in this effort were 2505, 5005, 7505, 8338, and 10,005 Hz. The time these pulsing sequences were swept varied between 1, 2, 4, and 8 seconds. To establish the benefits of the FT-IMMS techniques utilized herein in combination with all the aspects of the system 100, the present techniques were compared with Signal averaging-IMMS (SA-IMMS). While exact matching of experimental lengths between the present FT-IMMS techniques and SA-IMMS was not always possible, all efforts were made to acquire data in the respective modes that enabled relevant comparison with respect to the number of averages so as to show enablement of the present application(s).

The length of data acquisition for both the Fourier and SA-IMMS experiments was adjusted between 1, 2, 4, 5, and 8 minutes although the embodiments are not limited to such time frames for data acquisition. Frequency scanning and waveform generation was accomplished using an Analog Discovery microcontroller (Digilent, Pullman, Wash.) capable of executing a frequency sweep and delivering the pulsing sequence as a TTL-compatible signal. In addition to the frequency sweep this unit also contained the built-in capacity to alter the phase and/or amplitude of the pulsing sequence.

Chemicals and Reagents

A range of tetraalkyimmonium salts (Sigma-Aldrich, St. Louis, Mo.) were used to evaluate the performance of the FT-IMMS technique relative to the signal averaging experiments. More specifically, the following salts were used throughout this study: tetrapropylammonium bromide (T3A, m/z 130.1596), tetrabutylammonium bromide (T4A, 20 m/z 242.2848), tetrahexylammonium bromide (T6A, m/z 354.4100), tetraheptylammoni-um bromide (T7A, m/z 410.4726), tetraoctylammonium bromide (TBA, m/z 466.5352), tetradecylammonium bromide (T10A, m/z 578.6604), tetradodecylammonium chloride (T12A, m/z 690.7856). A shorthand notation for each quaternary ammonium cation was adopted with the number indicating the number of carbons in each side chain. Because only the cation was observed in the current study, the m/z listed for each analyte corresponds to the accurate mass of only that species and not the molecular weight of the full salt including the halide anion.

Used without any further treatment, individual 50 µM solutions of these salts were made in a 50:50:0.1 mixture of acetonitrile, water, and formic acid (FA), respectively. From these stock solutions, a mixture containing all of the quaternary ammonium salts was constructed with concentrations range from ~100 nM to 5 µM. This range was chosen to explore the ability of the system to capture information on analytes in mixtures of varying concentration. These samples diluted in 50:50:0.1 ACN:H2O:FA were infused into the electrospray unit using a syringe pump (KD Scientific,) at 3 µL/min held at ~2800 V above the entrance to the IMS desolvation region 108, as shown in FIG. 1.

Pulse Design, Signal Processing, and Data Transformation/Results

The example techniques/embodiments herein utilize a customized approached to data acquisition for FT-IMMS and Hadamard-IMMS in addition to other transform techniques capable of being coupled with the modulation methodologies herein. It is to be appreciated that a discrete on/off cycling of the BN-gate(s) is necessary for the Fourier transformation (e.g., FT-IMS) implementation herein and thus the basic windowing function used to recover data in the mobility domain was based upon a rectangular pulsing scheme provided as the gating function.

This direct treatment of the data prior to performing a Fourier transform often produces a range of ringing artifacts due to the discrete truncation of the signal (i.e., truncated sine and cosine functions). As somewhat stated in the background section, signal recovery apodization functions have thus historically been applied when using such conventional FT-IMS techniques. However, these functions also discard real signals to minimize the contributions of transform noise.

Figure 2:
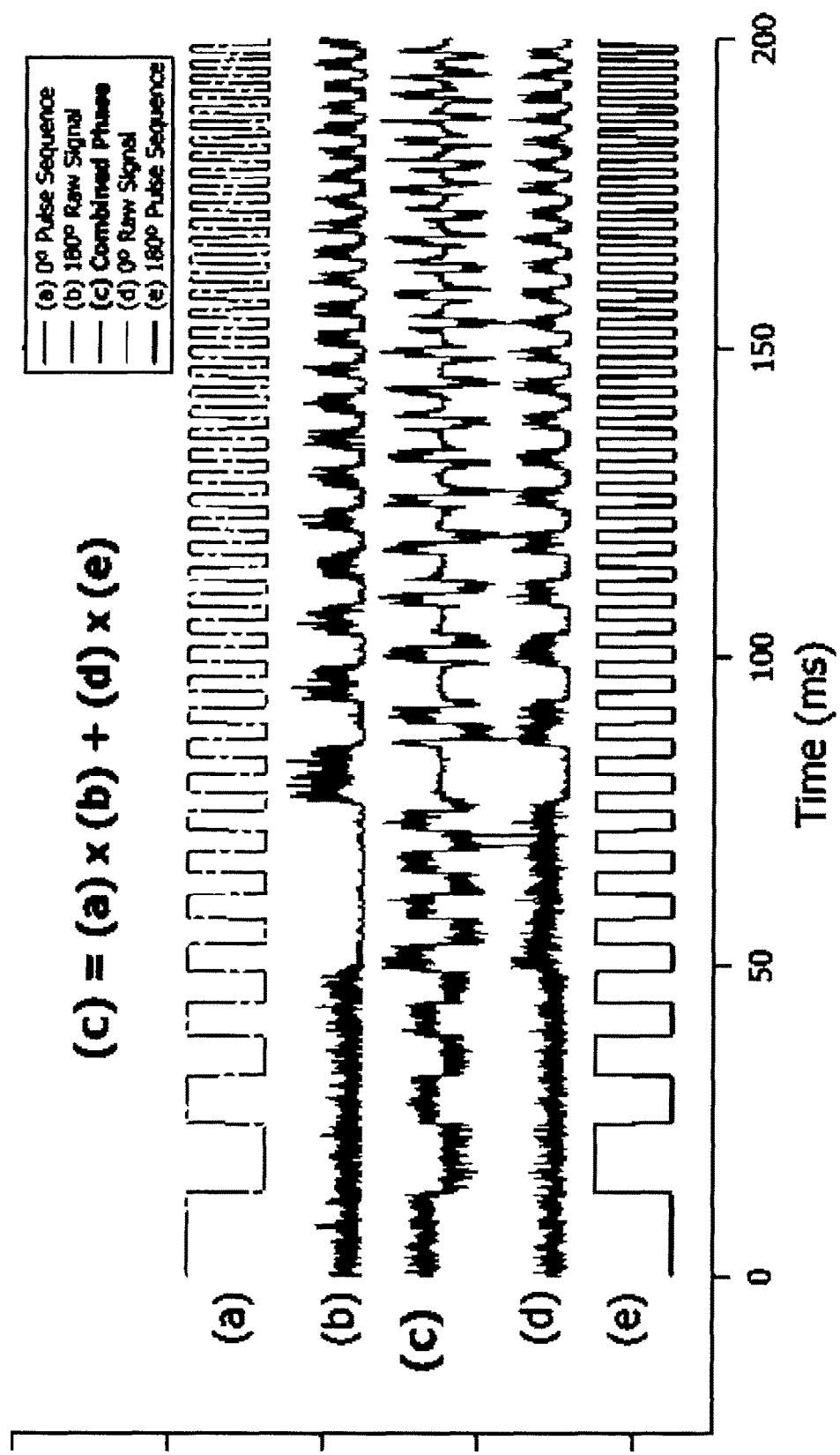
FIG. 2 shows an FT-IMMS multiplexing scheme that combines the raw time-domain data from two different pulsing schemes that are 180° out of phase.

The reader is now directed to FIG. 2 and the following discussion for the sequence utilized herein for the implementation of the present FT-IMMS methodology. In particular, FIG. 2 shows an FT-IMMS multiplexing scheme that combines the raw time-domain data ((b) and (d)) from two different pulsing schemes that are 180° out of phase ((a) and (e)). This experimental sequence is followed to obtain a raw combined phase spectrum (c) suitable for transformation into the frequency domain which contains mobility data. By combining the two signal traces originating from the two pulse phases, transform artifacts are greatly minimized.

It is to be noted that FIG. 2 only shows the first 200 ms of a frequency sweep ranging from 5-7505 Hz over the course of 2 seconds, and thus serves to highlight, but not in a limiting fashion, the multi-step experimental process necessary to recover mobility spectra from the multiplexed experiment without apodization.

The plot denoted as (a) in FIG. 2 corresponds to the linear frequency sweep applied to the BN gate 110 of FIG. 1 and is denoted as the 0° pulsing sequence. This sequence initiates the experiment with the BN gate 110 in the open configuration and proceeds through the frequency sweep with a 50% duty cycle. Using the TOF-MS 102 as a detector, the raw data in the time-domain was extracted based upon a specific range of m/z values. The plot denoted as (b) in FIG. 2 represents the raw, unsmoothed signal data for T8A at m/z 466.5 that correspond to the 0° pulsing sequence shown in plot (a) of FIG. 2. It should be noted that a discrete transformation of these data result in an observable mobility peak but with significant ringing due to the truncation of the signal for the closed gating cycle.

In many ways, the ideal time-domain signal approaches a free-induction decay (FID) similar to the spectral themes observed in NMR and Fourier transform ion cyclotron experiments. However, in order to achieve such a result for a FT-IMMS setup a complementary signal set is required. This result can be attained by operating the frequency sweep in a novel manner 180° out of phase relative to the initial pulsing sequence.

The plot denoted as (e) in FIG. 2 outlines the pulse sequence that accomplishes this goal relative to the plot denoted as (a) in FIG. 2 and note that it also produces a characteristic time-domain signal (see plot (d)) that when transformed produces signal ringing in the frequency domain. To avoid confusion, plot (d) in FIG. 2 is derived from the application of the pulsing sequence shown in plot (e) in FIG. 2 to show the algorithmic approach used to arrive at the combined signal shown in plot (c) shown in FIG. 2.

In particular, the combined phase data to provide for the data in plot (c) shown in FIG. 2 represents a direct approach without apodization that effectively fills the gaps in the raw data that would otherwise be observed as zeros and establishes the condition conducive to ringing upon transformation. In many ways this is a direct means of efficiently simulating a second ion gate algorithmically.

Figure 3:
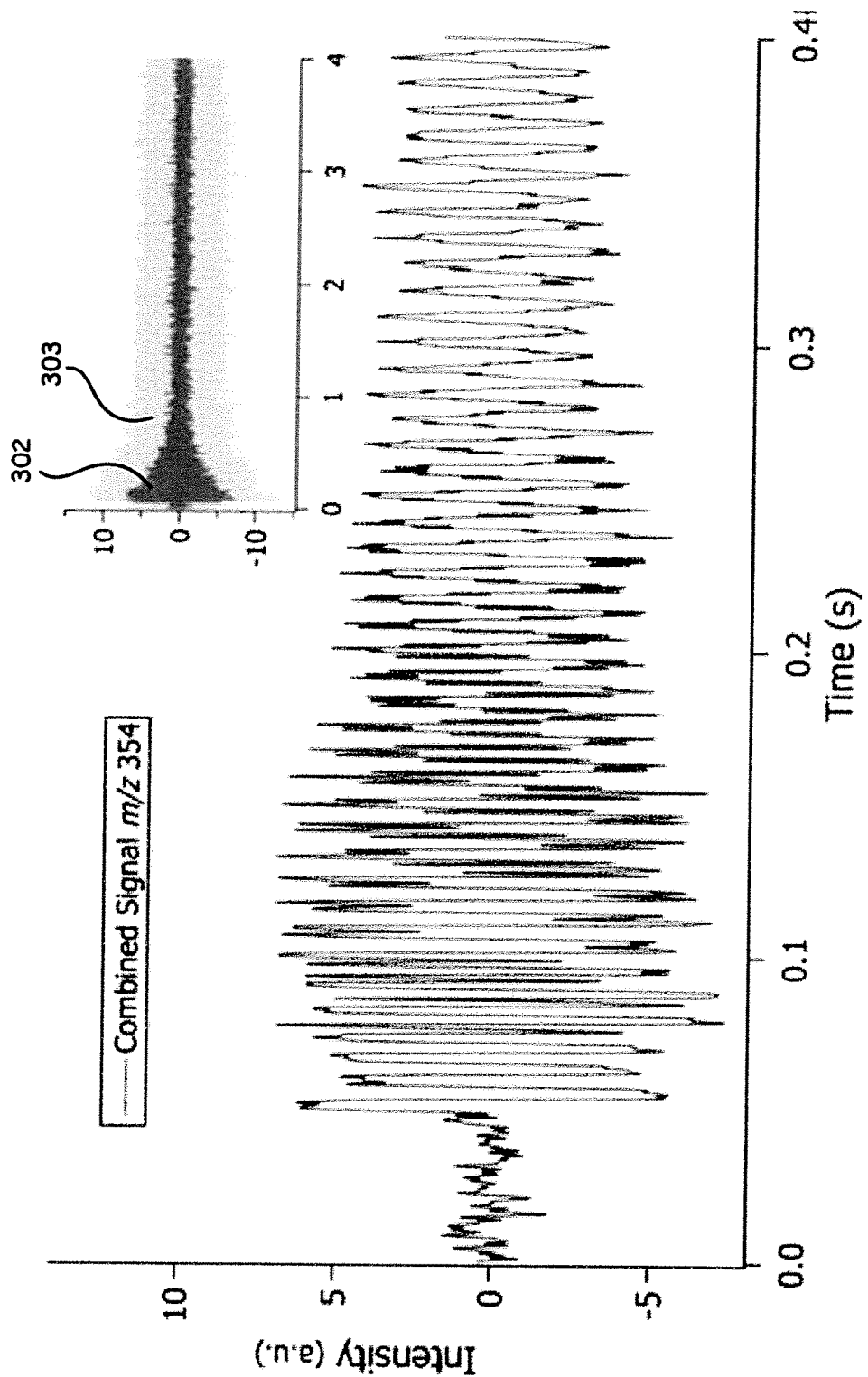
FIG. 3 shows combined phase time domain data resulting from the scheme outlined in FIG. 2.

When the raw data from the two-data are combined they result in a signal that largely adopts the shape of FID and is centered about 0. FIG. 3 highlights such a result and represents the experimental scheme shown in FIG. 2 but for T6A and a sweep time of 4 s and a maximum frequency of 8338 Hz or ½ the frequency of the TOF-MS system acquisition rate. In particular, FIG. 3 shows the combined phase time domain data shown in the main figure of FIG. 3 resulting from the scheme outlined in FIG. 2. Thus, the data in the main figure correspond to data extracted for the T6A ion (m/z 354) with only the first 400 ms being shown. The total frequency sweep time for these data was 4 seconds, as shown in the top right inset. For display purposes, the dark traces 302 in the inset figure were smoothed using a 25 point binomial function, while the semitransparent trace 303 corresponds to the raw data. For all transformed data and comparisons shown herein, only raw, unsmoothed data were used.

Following the experimental steps outlined in FIG. 2 discussed above, raw mobility signals in the time domain may be constructed for each m/z similar to the spectrum shown in FIG. 3. Though the main trace shown in FIG. 3 has been smoothed using a binomial function, only the raw data were used for SA-IMS comparison. These raw data and full FID for the T6A are shown within the inset of FIG. 3.

The smoothed traces 302 in FIG. 3 are presented to highlight spectral features with all other traces 303 corresponding to the raw signal. Transitioning from the raw data shown in FIG. 3 spectra to traditional DT-IMS may be constructed through the application of a transform methodology, such as, but not limited to, the Fast Fourier transform (FFT).

Figure 4:
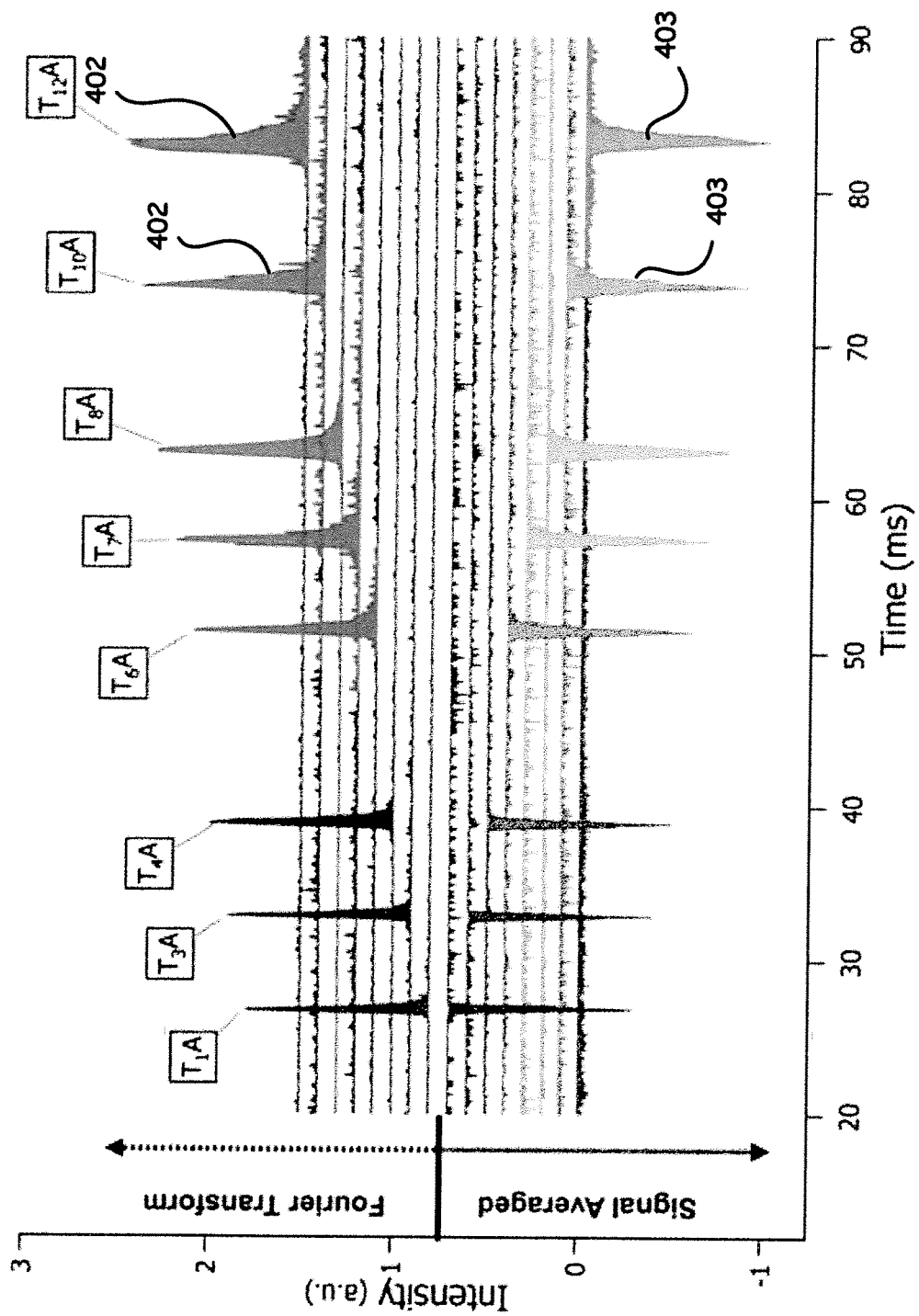
FIG. 4 shows direct spectral comparison between FT-IMMS experiments and SA-IMMS data for all of the TXA salts examined. Positively oriented peaks correspond to the FT-IMMS results while the inverted peaks originate from signal-averaged results

FIG. 4 shows direct spectral comparisons between FT-IMMS experiments and SA-IMMS data for all of the TXA salts examined. Positively oriented peaks 402 (two peaks denoted for simplicity) correspond to the FT-IMMS results while the inverted peaks 403 (two peaks again denoted for simplicity) originate from the signal-averaged results (240 µs gate pulse width). These data illustrate the improved signal-to-noise ratios afforded by the FT-IMMS technique. Though many different parameters may be adjusted for the FT-IMMS experiment, the data provided in this figure were derived for a 4 second sweep spanning 8338 Hz. The FFT used to produce the transformed spectra in FIG. 4 is a multidimensional prime factor decomposition derivative of the Cooley-Tukey algorithm (IGOR Pro, Wavemetrics, Lake Oswego, Oreg.). Positive trending peaks correspond to the FFT of the raw signal for each TXA salt, whereas the negative trending peaks were obtained using the signal-averaging mode. The inversion of peaks was conducted only for presentation purposes and the stacked plot also aids in the visual inspection of the range and type of noise observed for each operational mode.

In discussing the figures of merit related between the two modes of operation the application herein first addresses the systematic frequency shift observed with the FT-IMMS experiment. Using a standard two-gate system to acquire FT-IMS data, the mechanism to recover drift time is achieved by dividing the experimentally measured frequency (i.e. result following FFT) by the sweep rate in Hz/s. This step produces a spectrum with peak locations that directly correspond to the IMS drift times simply because the two-gate configuration explicitly defines the drift region. In the case of FT-IMMS using a TOF-MS 102 shown in FIG. 1, there are additional, though comparatively small, contributions to the recorded time that correspond to ion flight times that are not governed by mobility. Typically ion transit times in the compact TOF-MS 102, including the m/z separation, are up to a few hundred microseconds. These contributions do not shift the overall drift time significantly but can contribute to the errors in mobility calculations.

In addition, a bias is associated with the applied frequency sweep rate. All linear sweep experiments across 1, 2, 4 and 8 seconds exhibited a systematic bias towards larger frequencies upon transformation using the scheme outlined in FIG. 2. Because the shift observed was toward higher frequency, its origins are believed to arise from another highly deterministic error. By directly comparing experimentally determined signal-averaged drift times with those measured using the FT-IMMS system 100, a Pearson's coefficient of linearity ($R^2$) of 0.9983 was determined. Using this relationship, the measured frequencies were shifted according to the apparent bias induced by the hardware employed in this work. Following this correction, the average percentage deviation in observed drift times for the FT-IMMS was 0.020+/−0.77% compared to SA-IMMS experiments.

Evaluation of Transformed Signal to Noise Ratio

Figure 5:
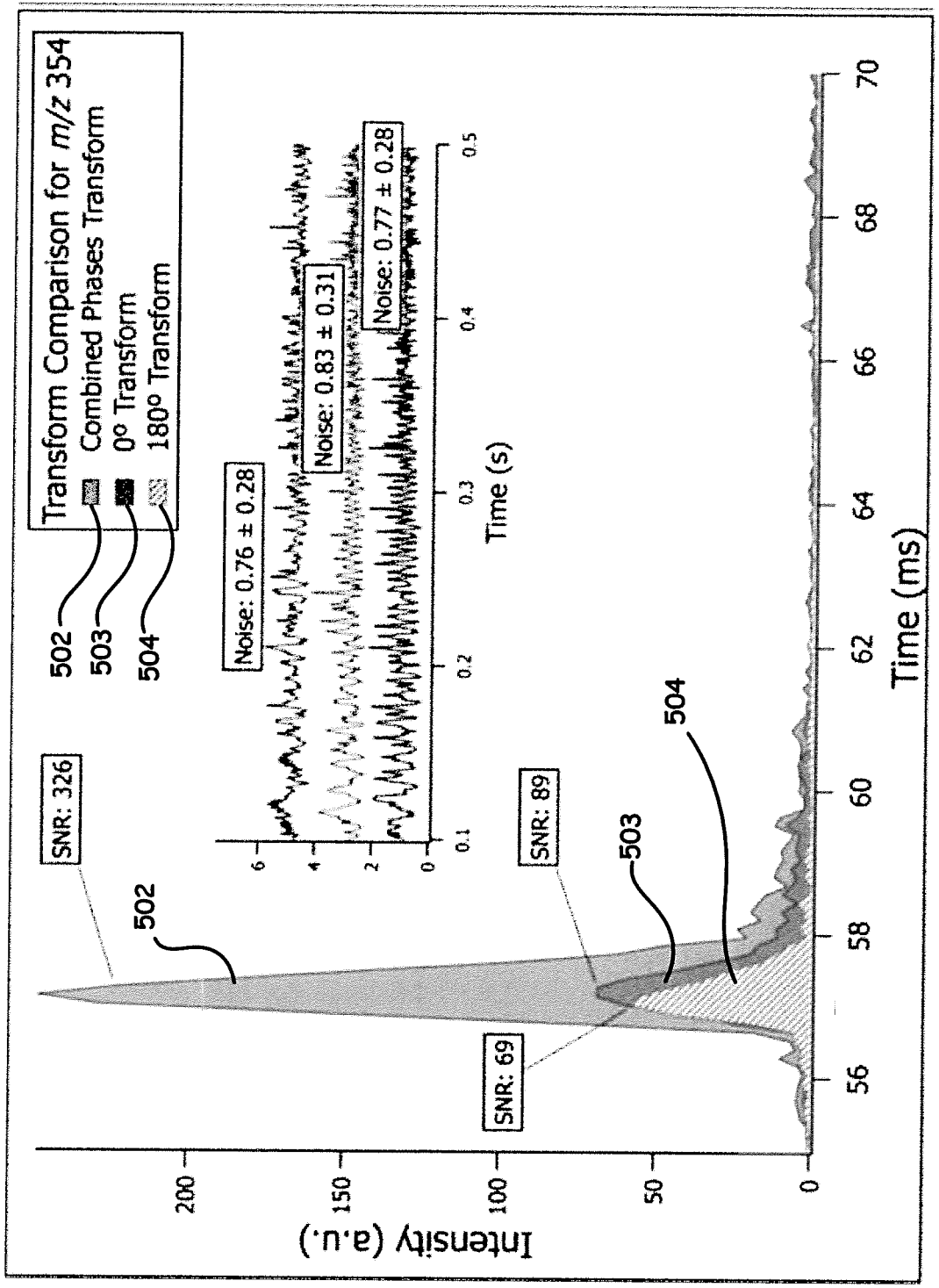
FIG. 5 shows that while possible to transform the raw data from individual signal chirps, the combined phase data shown in FIG. 4 indicates a marked improvement in signal to noise ratio even when doubling the acquisition time for a single phase.

Accordingly, the scheme shown in FIG. 2 requires the acquisition of two data sets prior to applying, for example, an FFT. Because this additional spectrum doubles the required experiment time, comparisons to single phase FT-IMMS experiments must be adjusted by this factor. FIG. 5 shows the result of three representative transformations for the T6A signal including the 0° (denoted by reference numeral 503), 180° (denoted by reference numeral 504), and combined phase data sets (denoted by reference numeral 502).

In particular, FIG. 5 shows that while it is possible to transform the raw data from individual signal chirps, the combined phase data shown in FIG. 4 indicates a marked improvement in signal-to-noise ratio even when doubling the acquisition time for a single phase. Transformed data for each individual phase and their combination is shown. The inset shown for longer times highlights the common noise characteristics observed including the periodic contributions from 120 Hz 30 noise. The SNR was calculated by measuring the standard deviation of the noise across a range expected to be absent of ions (i.e. 10-20 ms), multiplying this value by 3, and comparing this to the maximum signal intensity for a given peak. The SNR for the three different transforms 502, 503, and 504 shown in FIG. 5 highlights the clear benefit afforded by the combining of the different phases.

The SNR for the 0° 503, 180° 504, and combined signals 502 are indicated in FIG. 5 as 69, 89, and 326 respectively. Based upon the principles of signal averaging, doubling the experiment time to match the time required to produce the combined signal would maximally increase the SNR by a factor of $\sqrt{2}$. Even for the best SNR result from a signal phase FT-IMMS experiment, this only leads to a maximum SNR of 125 which differs from the combined phase approach by more than a factor of 2.5. Another interesting, yet unexploited, feature in the datasets shown is the periodic signals also found in the noise. Closer examination of the spectral regions that do not contain well-defined mobility peaks (i.e., inset of FIG. 5) highlights the appearance of a cyclical noise component that corresponds directly to 120 Hz noise. A surprising and beneficial observation was that the combined phase aids in reducing this noise component because the times at which each phase of the experiment is initiated differ. The increase in overall SNR observed for the combined-phase FT-IMMS approach is derived from the increased number of resonant ion beats observed at the detector. Another interesting aspect of the combined approach is the small, yet consistent shift in the drift times between the individual and combined phase results.

The combined phase transform yields a peak centroid that is always between the value observed for 0° and 180° transformed results. Though a minor correction, the combined phase approach aids in a more accurate reflection of drift time using FT-IMMS approaches. Using the approach to calculate SNR for FIG. 5, the SNR for T4A, T8A, and T12A across a range of frequencies and sweep times is shown in FIG. 6.

Figure 6:
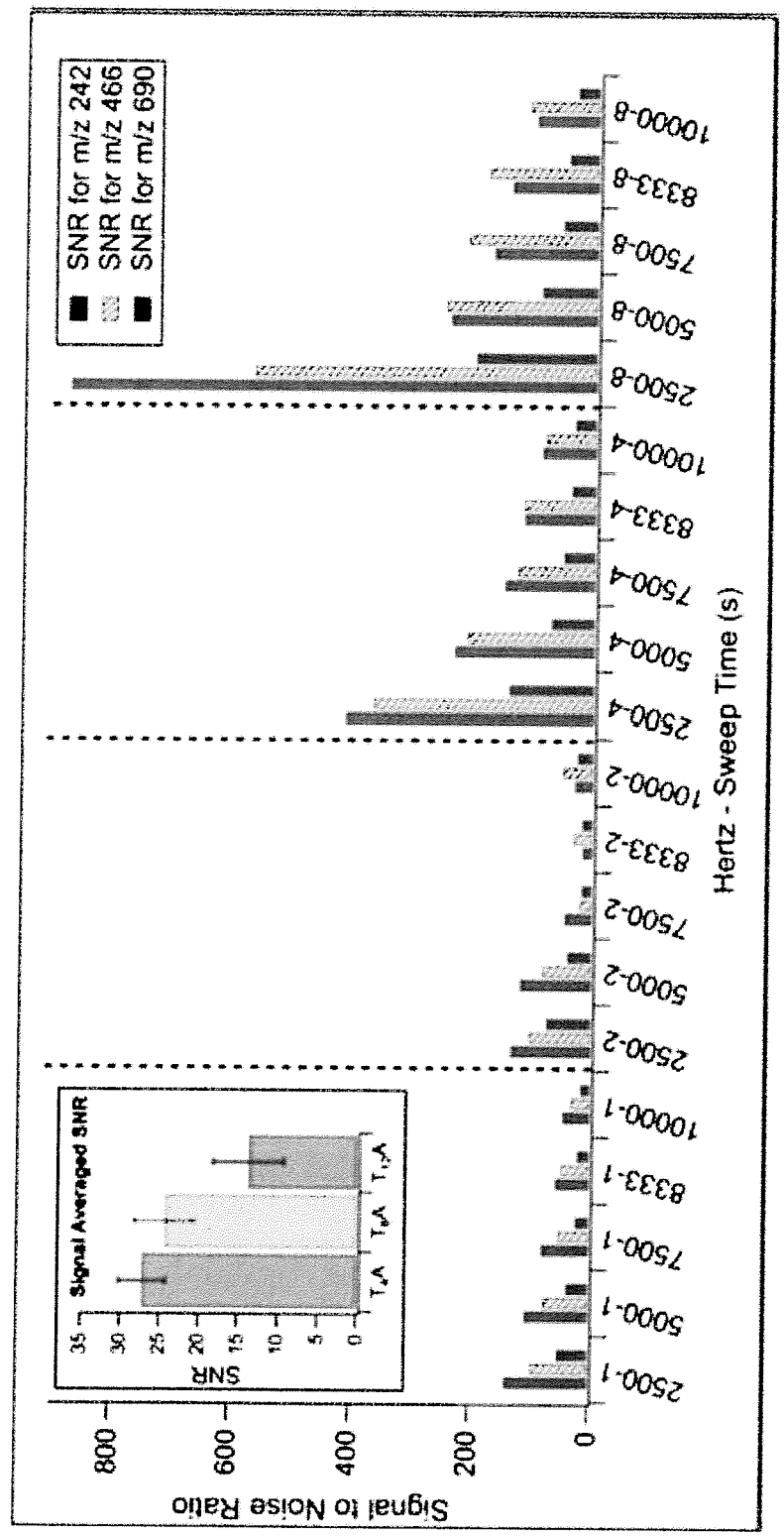
FIG. 6 shows impact of sweep time and frequency range on signal-to-noise ratio (SNR) for 3 of the 9 TXA salts examined. For comparison the figure inset provides the SNR observed for the SA-IMMS data. Maximum FT-IMMS SNR was observed from longer sweep times which is directly related to the number of well-resolved resonant ion beats found in the raw data.

FIG. 6 thus shows the impact of sweep time and frequency range on signal-to-noise ratio (SNR) for 3 of the 9 TXA salts examined. For comparison, the figure inset provides the SNR observed for the SA-IMMS data. Maximum FT-IMMS SNR was observed from longer sweep times which are directly related to the number of well-resolved resonant ion beats found in the raw data. FIG. 6 thus captures the SNRs observed for each of the target TXAs as a function of both sweep range and time, and for comparison, equivalent SA-IMMS SNRs are shown as a subplot. To minimize the impact of differing averages, all of the data in FIG. 6 were acquired for 2 minutes and the SA-IMMS data sets originated from experiments using a 240 µs gate pulse width and 90 ms scan times.

In all combinations of sweep times and frequency ranges the FT-IMMS experiments yielded SNRs that exceeded the SA-IMMS data sets. For the extended sweep times (i.e. 8 seconds) even with the same 2 minute acquisition time, the SNR gain for the FT-IMMS experiments were often an order of magnitude greater than the signal-averaged data. However, this trend was not always true for the T12A species which did not exhibit the large SNR gains for higher sweep frequencies. This again is attributed to the reduced numbers of resonant ion beats that are observed in the raw data sets because a shorter amount of time is spent on the resonant frequencies for faster sweep times.

There may be a temptation to interpret the observed changes in SNR as a function of m/z, however, the absolute concentrations of the different species were chosen to compensate for differences in ionization efficiencies. Long sweep times and lower terminal frequencies produced the largest SNR gains, however as FIG. 7 illustrates, reduced frequency ranges rarely yield spectra with the highest resolving power.

Evaluation of Multiplexed Resolving Power

Figure 7:
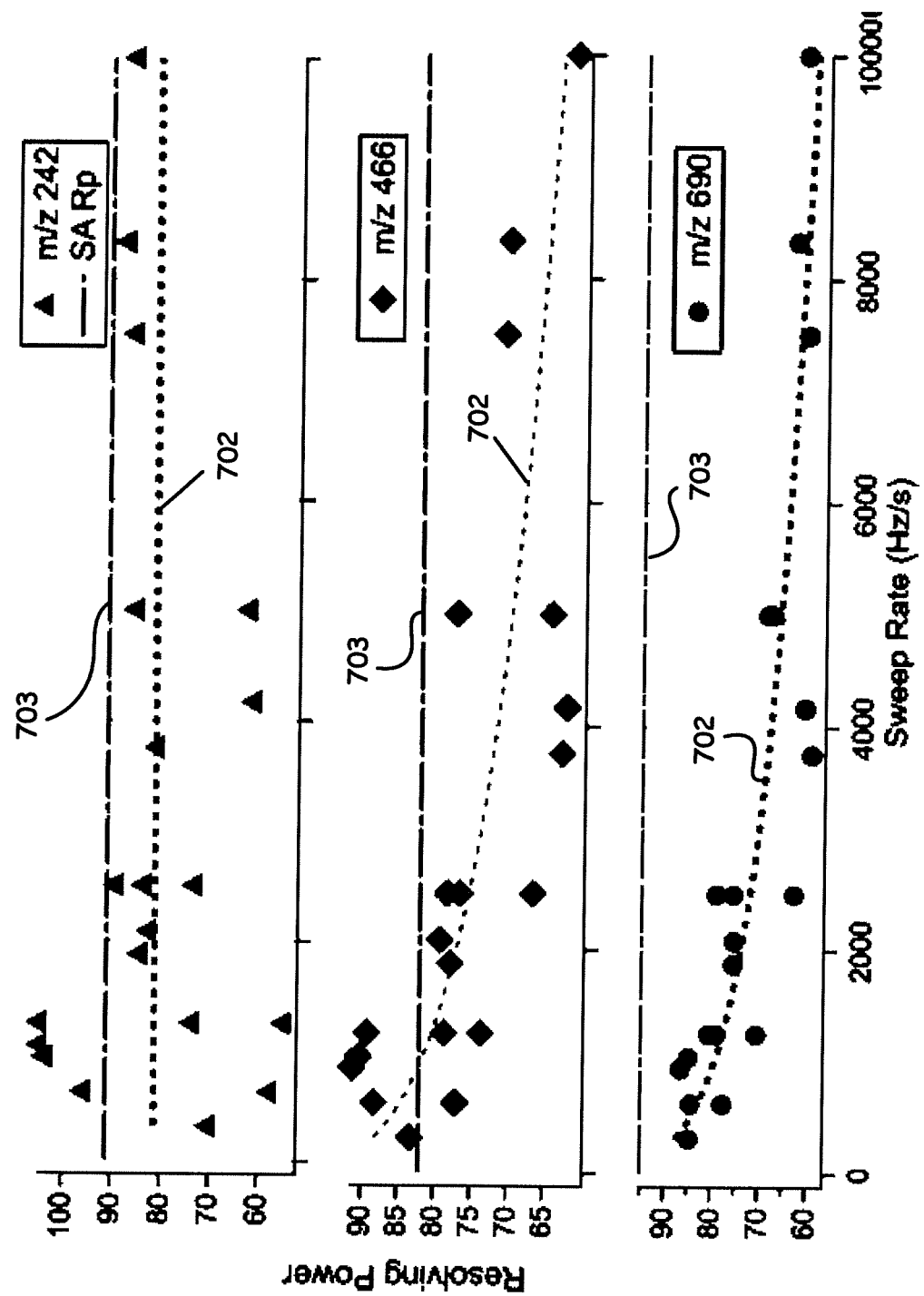
FIG. 7 shows a resolving power comparison between different experimental variables for the FT-IMMS experiment.

FIG. 7 provides a resolving power (Rp) comparison between the different modes of analyses for 3 representative TXAs (T4A, T8A, and T12A). In particular, FIG. 7 shows a resolving power comparison between different experimental variables using the FT-IMMS system shown in FIG. 1. For the 3 TXAs shown (T4A, T8A, and T12A) the signal averaged resolving power is highlighted as a straight horizontal line. Shorter frequency ranges and sweep times yielded the lowest resolving power for the FT-IMMS experiment. Resolving powers that exceeded the SA-IMMS data were routinely observed for broader frequency sweeps and sweep times of 8 seconds.

As with the SNR comparison, the frequency sweep range and time influences the resulting mobility spectra and it was for this reason that Rp of each spectrum was plotted as a function of sweep rate (Hz/s). The highly dashed line 702 highlights data from the FT-IMMS data while the less dashed 703 line corresponds to the SA-IMMS data. This latter plot (i.e., data denoted as 703) highlights a general trend that SA-IMMS data provided modestly higher resolving powers than the multiplexed modes, but a more detailed examination of the data illustrate a more complex relationship for the FT-IMMS experiments.

Because these data are plotted as a function of sweep rate, there are FT-IMMS results that were acquired using the same frequency range but result in data points at the extremes of the axes shown. For example, a spectrum resulting from a 10 kHz sweep over 1 second yields FT-IMMS data points that are located to the far right of each plot while the same frequency range swept for 8 seconds produced data points with an x-axis value of 1250 Hz/s.

Using FIG. 1 and FIG. 2 as reference, the fidelity of the IMS peak from each frequency sweep is largely due to the number of resonant ion beats that are accurately recorded during the experiment. For high sweep rates the time the ion gate is cycling at any given frequency is shortened, which in turn reduces the number of resonant ion packets that are available. It is this trade-off that produces the characteristic decline in FT-IMMS resolving power at higher sweep rates. It is to be noted that in all cases shown in FIG. 7, the highest resolving power for the FT-IMMS spectra was obtained for 8 second sweep times while the lowest resolving power was generally obtained for 1 second sweep times. This result is in direct contrast to the SNR result which again highlights the trade-off inherent in this technique.

Another relevant comparison between the SA-IMMS and FT-IMMS is the degree to which each approaches the theoretical resolving power predicted by a standard application of diffusion rates. For the SA-IMMS data shown in FIG. 7 the Rc for T4A, T8A, and T12A were 93, 105, and 109 respectively. These values were calculated using values of 690 Torr, 493 Kelvin, 250 V/cm and a 240 μs gate pulse width, and the reported reduced mobilities for the target TXA salts. For the T4A ion the measured resolving power reached 98% of the theoretical maximum (i.e. Rc) while the T12A species only reached 87% of the theoretical maximum for that species. The approach calculating Rc for the FT-IMMS experiment is thus directly related to the maximum frequency swept.

For example, frequency sweeps that end at 10 kHz result in a BN gate 110 50% duty cycle that alternates between on and off states every 100 μs. Alternatively, conditional resolving power estimations for FT-IMMS experiments terminating at 4,167 Hz would be equivalent to a SA-IMMS experiment using a 240 μs gate pulse width. While that specific frequency was not chosen for the FT-IMMS experiments, the outlined herein data were acquired for terminal frequencies of 5005 Hz. For those FT-IMMS data sets (equivalent to 200 μs SA-IMMS experiments), the experimentally observed resolving powers achieved between 86 and 98% of the predicted Rc values. This range is due to a number of factors including the speed at which ions traverse the ion gating region and the depletion of the ion population that occurs as the ion gate returns to the closed state.

The combined impacts of gate depletion and the increasing frequency of ion gating cycling establish conditions for the decay of the FT-IMMS signal. This behavior is not entirely surprising but also sets the stage for the inverse transform necessary to recover the original IMS peak. Another factor that also contributes to some of this resolving power variability is the use of a time-to-digital converter rather than an analog-based acquisition system. It is thus to be reiterated that the maximum Rp for the FT-IMMS experiments was for the 8 seconds sweep times and it is our assertion that this observation is due to the increased numbers of resonance ion beats that may be observed for longer sweep times. This final observation regarding resolving power is based upon a general trend of increasing resolving power with decreasing analyte drift time (data not shown). Stated differently, higher FT-IMMS resolving powers were observed for ions with higher mobilities (shorter drift times) regardless of the frequency range swept.

Accordingly, by modulating an ion beam in an ion mobility time of flight system using two frequency chirps oriented 180° out of phase, a new FT-IMMS approach that enhances both SNR, ion throughput, and does not require any hardware modifications is enabled. Initial evaluations of the FT-IMS approach illustrated modest gains in signal-to-noise ratio (SNR) when compared to signal-averaged IMS experiments (SA-IMS) with maximum realized gain factors of ~3. The inability of previous systems to fully realize multiplexing gains is attributed to a number of factors including the need for two physical ion gates and most importantly the need for apodization function to recover IMS spectra from raw frequency-encoded ion signals.

In contrast, the two-phase FT-IMMS technique disclosed herein utilizes in a novel manner only a single ion gate and requires no apodization functions to reconstruct drift time. This latter benefit is a direct result of combining the data from the two respective pulsing phases. Moreover, the present techniques disclosed herein can be achieved without any advanced signal processing steps (e.g. smoothing or matched filtering) to routinely provide for up to an order of magnitude in gain and even greater in SNR for the FT-IMMS technique compared to the traditional signal-averaged mode of operation. Lastly, the SNR gains afforded by the two-phase FT-IMMS approach are readily achievable using any standard DT-IMMS and the ultimate performance is only limited by the maximum frequency at which the ion gate may operate effectively and the sampling rate of the detector.

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention.

The invention claimed is:

1. A method for ion populations analysis, comprising:
obtaining a first data set that further comprises:
modulating a single ion gate with a first binary On-OFF frequency sweep across a range of frequencies, and
acquiring a first raw data in the time domain at a detector from ion current resulting from the first binary On-OFF frequency sweep,
obtaining a second data set that further comprises:
modulating the single ion gate with a second binary On-OFF frequency sweep across a range of frequencies, wherein the second binary On-OFF frequency sweep is 180° out of phase from the first binary On-OFF frequency sweep, and
acquiring a second raw data in the time domain from received ion current resulting from the second binary On-OFF frequency sweep; and
combining the first and the second data set to provide for raw mobility signals of the ion populations in the time domain for each mass-to-charge (m/z) over a range of selected m/z values,
wherein the range of selected m/z values to obtain each m/z of the ion populations is provided by a hybrid ion mobility mass spectrometer.

2. The method of claim 1, wherein the combining step further includes utilizing a mathematical transform of the raw mobility signals.

3. The method of claim 2, wherein the mathematical transform is at least one transform selected from a Fourier transform, a Fast Fourier transform (FFT), and a Hadamard transform.

4. The method of claim 2, after transform of the raw mobility signals into one or more measured frequencies, the method further comprises: dividing the one or more measured frequencies by the sweep rate in Hertz/seconds (Hz/s) so as to provide a spectrum with peak locations directly corresponding to the drift times within a configured ion mobility spectrometer.

5. The method of claim 1, where the first and the second binary On-OFF frequency sweeps are provided from a lower frequency limit to an upper frequency limit over a sweep time as determined by a resolving power and/or a sensitivity criteria.

6. The method of claim 5, wherein the first and the second binary On-OFF frequency sweeps increases linearly to the upper frequency limit.

7. The method of claim 5, wherein the first and the second binary On-OFF frequency sweeps changes nonlinearly between the lower frequency limit and the upper frequency limit.

8. The method of claim 5, wherein at least one of amplitude and phase of the first and the second binary On-OFF frequency sweeps changes between the lower frequency limit and the upper frequency limit.

9. The method of claim 5, wherein the first and the second binary On-OFF frequency sweeps are in a range of between 5 Hz up to 10 kHz.

10. The method of claim 1, wherein the first and the second binary On-OFF frequency sweeps are configured as a multiplexed two-phase approach to provide for a 50% duty cycle of the generated ion populations.

11. The method of claim 1, wherein modulating the single ion gate in obtaining the second data set simulates a second ion gate configured within an ion drift region of an ion mobility spectrometer.

12. The method of claim 1, wherein the mass spectrometer is at least one mass analyzer selected from the group consisting of a quadrupole mass analyzer, a two-dimensional ion trap, a three dimensional ion trap, and a time-of-flight (TOF) analyzer.

* * * * *